(12) United States Patent
Sutton et al.

(10) Patent No.: US 6,533,750 B2
(45) Date of Patent: Mar. 18, 2003

(54) CONICALLY SHAPED PHACO TIP

(75) Inventors: Thomas B. Sutton, Irvine, CA (US); Kenneth E. Kadziauskas, Las Flores, CA (US)

(73) Assignee: Advanced Medical Optics, Santa Ana, CA (US)

( * ) Notice: Subject to any disclaimer, the term of this patent is extended or adjusted under 35 U.S.C. 154(b) by 0 days.

(21) Appl. No.: 09/767,436

(22) Filed: Jan. 23, 2001

(65) Prior Publication Data

US 2002/0099325 A1 Jul. 25, 2002

(51) Int. Cl.$^7$ .................. A61B 17/20; A61B 17/32; A61M 1/00; A61M 3/00; A61M 5/00
(52) U.S. Cl. .................. 604/22; 604/27; 604/35; 604/43; 604/187; 604/239; 604/264; 606/167
(58) Field of Search .................. 604/19, 22, 27, 604/35, 43, 44, 164.01, 187, 239, 264, 272–274, 540, 542, 902; 606/167–169, 171

(56) References Cited

U.S. PATENT DOCUMENTS

| | | | |
|---|---|---|---|
| 4,297,886 A | * 11/1981 | Anikeev et al. | 73/642 |
| 4,808,153 A | 2/1989 | Parisi | 604/22 |
| 4,816,018 A | 3/1989 | Parisi | 604/22 |
| 5,213,569 A | 5/1993 | Davis | 604/22 |
| 5,242,385 A | 9/1993 | Strukel | 604/22 |
| 5,451,229 A | 9/1995 | Geuder et al. | 606/107 |
| 5,653,724 A | * 8/1997 | Imonti | |
| 5,989,209 A | * 11/1999 | Barrett | |
| 5,993,408 A | 11/1999 | Zaleski | 604/22 |
| 5,993,409 A | * 11/1999 | Maaskamp | |
| 6,007,499 A | * 12/1999 | Martin et al. | 601/3 |
| 6,007,555 A | * 12/1999 | Devine | |
| 6,039,715 A | 3/2000 | Mackool | 604/272 |
| 6,159,175 A | * 12/2000 | Strukel et al. | |

OTHER PUBLICATIONS

Article: New Phaco Tip Geometry Balances Power, Suction from Ophthalmology Times dated Jul. 15, 1992.

* cited by examiner

*Primary Examiner*—Timothy L. Maust
*Assistant Examiner*—Anu Ramana
(74) *Attorney, Agent, or Firm*—Walter A. Hackler; Peter Jon Gluck

(57) ABSTRACT

A phacoemulsification needle includes a body having an aspiration lumen therethrough along with a hub disposed at a proximal end of the needle body for engaging an ultrasonic handpiece in order to couple ultrasonic energy into a needle body. A tip is provided at a distal end of the needle body for penetrating tissue to be emulsified and a conical ultrasonic surface disposed at the tip is provided for focusing ultrasound in tissue beyond an end of the tip in order to promote cavitation in tissue beyond the tip end. The conical ultrasonic radiation surface extends from the lumen to the end of the tip.

15 Claims, 2 Drawing Sheets

CONICALLY SHAPED PHACO TIP

The present invention generally relates to ultrasonic surgical instruments, and more particularly, relates to a needle specifically designed for promoting cavitation in eye tissue and for the removal of fragmented tissue from the eye.

Phacoemulsification involves utilization of a hand held microsurgical tool known as a phacoemulsification handpiece or probe. The phacoemulsification handpiece utilizes a small diameter needle with a tip that is designed for emulsifying, fragmenting and/or cutting tissue after it is inserted into an incision into the cornea or sclera of an eye.

The needle typically includes a central channel, or lumen, connected to a source of suction, which aspirates the emulsified, or fragmented, tissue from the eye.

The needle and tip is vibrated by an ultrasonic source and a hydrodynamic flow of a saline solution is established in order to prevent collapse of the eye interior chamber. As particles of cataract tissue are emulsified, cut, or fragmented from the cataract mass, the particles are removed from the chamber through the tip central lumen.

Many attempts have been made to improve the performance of the needle by way of enhancing the introduction of ultrasonic energy in order to provide cavitation of tissue to facilitate the fragmentation or emulsification thereof within the needle. Several types of needles have been developed, which include a design having a beveled or stepped edge in order to enhance the cutting efficiency of the cutting tip. Such as, for example, described in U.S. Pat. No. 5,993,408 to Zaleski.

Other developments include constant diameter needles having a tip wherein a forward projected surface at a beveled cutting edge is provided to enhance cavitation within the needle. See for example, a phaco tip geometry described in Ophthalmology Times V17 N14 P64 (Jul. 15, 1992). This article teaches a suction channel having a outward-tapering section that tapers conically in toward the suction channel toward the aperture at the tip of the needle.

This article asserts that a needle widening enables fragmentation of lens material with lower levels of power and permits higher suction pressures.

Further developments in needle tips include boring the tip to various sizes in a step-like progression as set forth in U.S. Pat. No. 5,451,229 to Geuder et al.

Unfortunately, none of the prior art has discovered the importance of emulsifying tissue particles before they enter the needle. The present invention is directed to the design of a needle tip with a radiation surface in order to enhance the efficiency of the needle tip by increasing a forward ultrasonic projection area of the needle.

SUMMARY OF THE INVENTION

Phacoemulsification needle in accordance with the present invention generally includes a needle body having a aspiration lumen therethrough and a hub disposed at a proximal end of the needle body for engaging an ultrasonic handpiece in order to couple ultrasonic energy to the needle body.

A tip is provided and disposed at a distal end of the needle body for penetrating tissue to be emulsified. The tip includes a larger diameter than a needle body diameter in order to provide for a conical ultrasonic radiation surface disposed at the tip for promoting cavitation in tissue forward of the needle tip. The conical ultrasonic radiation surface extends from the lumen to an end of the tip, that is, the conical surface intersects the end of the tip rather than an interior surface of the tip at a spaced apart distance from the end of the tip.

This structure causes a focusing of ultrasonic beyond the end of the tip and promotes cavitation of tissue particles before such tissue particles enter the needle. This prior cavitation significantly reduces the likelihood of plugging and/or clogging the aspiration lumen.

Importantly, the angle of disposition of the conical ultrasonic radiation surface is determined by maximizing the forward facing or focusing area of the interior of the tip. It has been found that the efficiency of ultrasonic radiation from the tip, which provides for forward cavitation, can be enhanced when the angle of radiation surface is selected in accordance with maximizing the forward focusing area within the geometrical constraints of a phaco tip. In this regard, the larger diameter of the tip enables a larger maximum diameter of the conical surface and a greater focusing area.

For example, the conical radiation surface may be disposed at an angle of between about 2 degrees and about 10 degrees with respect to a longitudinal axis of the needle body. Specifically, the ultrasonic radiation may be disposed at an angle of about 6 degrees with respect to the needle body longitudinal axis.

The present invention may also be defined as having a conical ultrasonic radiation surface of revolution which is disposed at the tip for promoting cavitation in tissue beyond the needle with the surface of revolution being established about a longitudinal axis of the needle body by a straight line extending between the lumen and a bitter end of the tip. The straight line intersecting between the longitudinal axis defines a disposition of the conical radiation surface which as hereinabove noted it may be between 2 degrees and about 10 degrees.

BRIEF DESCRIPTION OF THE DRAWINGS

The advantages of the present invention will be more clearly understood with reference to the following detailed description when considered in conjunction with the appended drawings of which.

DETAILED DESCRIPTION

Figure 1:
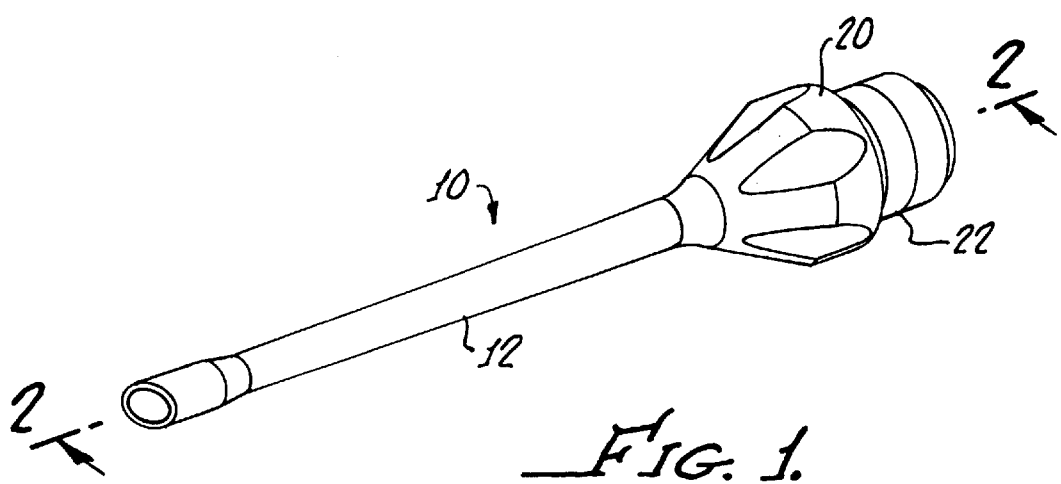
FIG. 1 is a perspective view of a phacoemulsification needle in accordance with the present invention.

With reference to. FIG. 1, there is shown a phacoemulsification needle in accordance with the present invention that may be formed from any conventional materials, as is well known in the art, for the manufacture of phacoemulsification needles.

Figure 2:
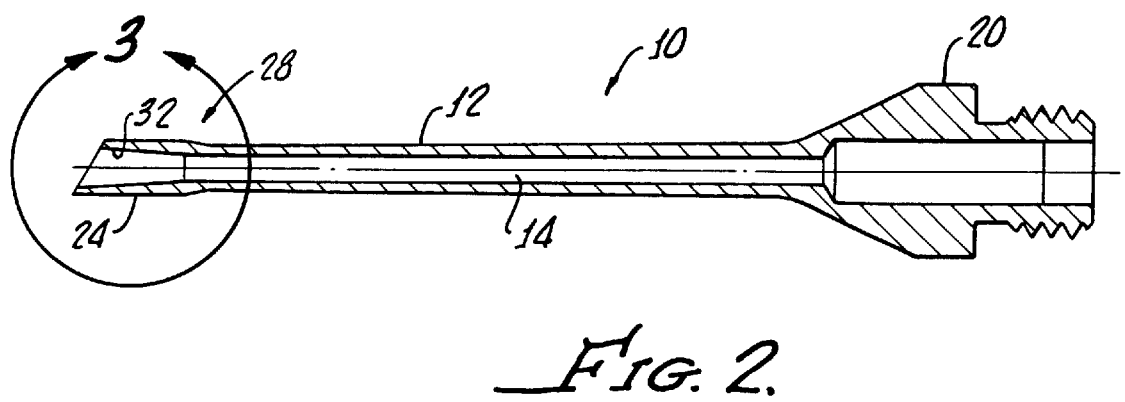
FIG. 2 in a cross-sectional view of the needle shown in FIG. 1 taken along the line 2—2.
Figure 3:
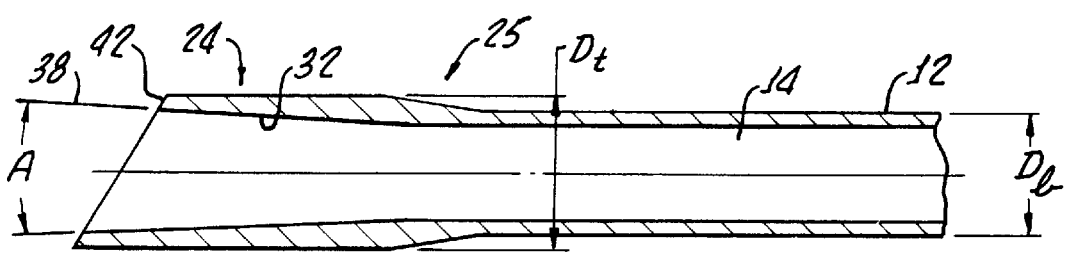
FIG. 3 in an enlarged view of the needle tip in accordance with the present invention as indicated by the section A as shown in FIG. 2, more clearly showing the angle of disposition of the conical radiating surface.

The needle 10 generally includes a needle body 12 with a lumen 14 therethrough for aspiration of fluid, see FIGS. 2 and 3.

A hub 20 is disposed at a proximal end 22 of the needle 10 for engaging an ultrasonic handpiece (not shown) in order to couple ultrasonic energy to the needle body 12.

A needle tip 24 is disposed at a distal end 28 of the needle body 12 for penetrating tissue (not shown) to be emulsified. Preferably, the tip 24 has a larger diameter $D_t$ than a diameter $D_b$ of the needle body 12.

For example, when the outside diameter $D_b$ of the needle body 12 is approximately 0.034 inches, the tip diameter $D_t$ may be about 0.042 inches. Despite this small increase in size, a significant advantages is provided by enabling the conical surface 32 to be formed within the tip 24.

The surface 32 may be defined as a conical ultrasonic radiation surface of revolution which is disposed in the tip 24 and established by a straight line 38 extending between the lumen 14 and an end of the tip 24. As a result of the increased or larger tip diameter, a larger maximum diameter of the conical surface is afforded which results in a larger forward focusing surface for radiation of ultrasonic energy.

The needle geometry of the needle body 12 is determined by a number of factors which include; incision site, flow characteristics, resonant frequency among others.

Preferably, the conical radiation surface 32 is disposed at an angle of between about 2 degrees and about 10 degrees, 10 degrees being the maximum practical interior angle. The exact angle of disposition A is determined by the interior and outer diameter of the tip and the required depth, which being dependent upon the hereinabove noted factors, can be adjusted so that the forward facing or focusing area is maximized.

Coordinating the conical body surface angle disposition with the needle geometry can result in an increase of forward focusing surface area efficiency of up to about 250%.

Figure 4:
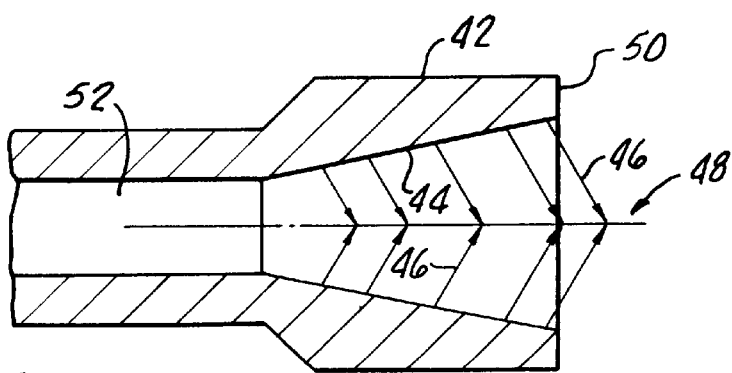
FIG. 4 is a cross-section of a tip in accordance with the present invention illustrating a focusing of ultrasonic energy beyond an end of the tip in order to fragment tissue before it enters the tip.

As shown in FIG. 4, a needle tip 42 in accordance with the present invention includes a radiating and focusing surface 44 which focuses ultrasonic energy, illustrated by the line 46 to a point 48 beyond an end 50 of the tip 42. This focusing causes cavitation and break up of tissue (not shown) before such tissue enters a needle tip lumen 52. Consequently, the likelihood of plugging or clogging the lumen is significantly reduced.

Figure 5:
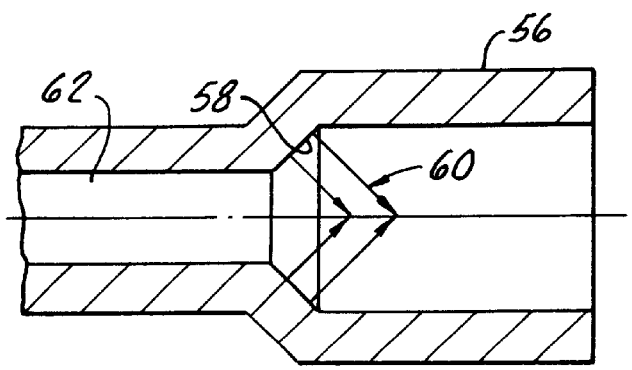
FIG. 5 is a cross-section of a prior art tip showing for comparison purposes, the focusing of ultrasonic energy within the prior art tip which can lead to clogging of an aspiration lumen passing through the prior art tip.

The surface 44 structure is to be compared to a prior art needle 56, shown in FIG. 5. In this instance, a focusing surface 58 causes a focusing of ultrasonic energy at a point 60 within the needle. The tissue is subjected to cavitation very close to the needle lumen 62, and consequently, clogging of the lumen 62 is more likely to occur.

Figure 6:
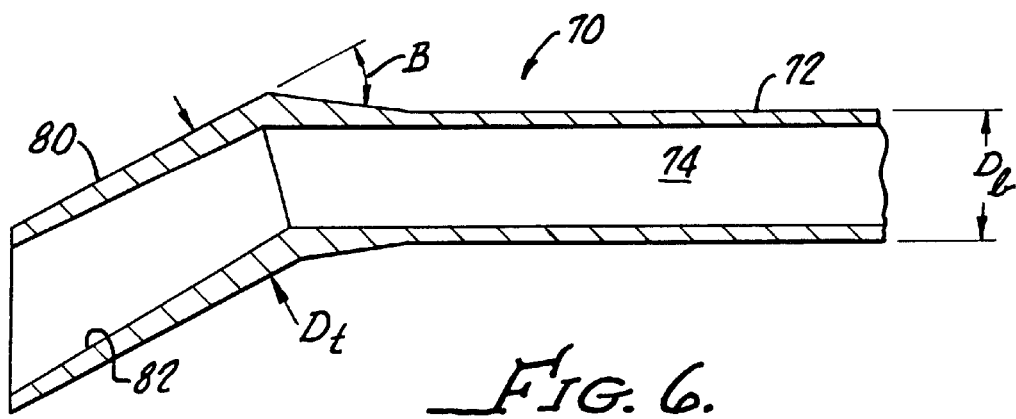
FIG. 6 is a cross-sectional view of an alternative embodiment of the present invention utilizing a needle tip disposed at an angle with a needle body.

Referring to FIG. 6 there is shown an alternative embodiment of a phacoemulsification needle 70 in accordance with the present invention which generally includes a straight needle body 72 having a lumen 74 therethrough for aspiration of fluid as hereinbefore described in connection with the needle 10 shown in FIGS. 1–3. The needle 70 includes an angulated tip 80 having a diameter $D_t$ greater than a diameter $D_b$ of the needle body 72 which provides for the advantages set for the in the description of needle 10.

The needle tip 80 is disposed at an angle B with respect to the needle body 72, which may be from about 0 degrees to about 45 degrees. This angulated tip has an advantage in reducing uncomfortable hand and finger positions of the surgeon when manipulating the needle tip 60 in a relation to a fixed corneal incision for bringing a conical surface 62 into a proper "head-on" position for breaking up the lens tissue in the inherently confined spatial areas involved (not shown).

Although there has been hereinabove described a phacoemulsification needle in accordance with the present invention for the purpose of illustrating a manner in which the invention may be used to advantage, it will be appreciated that the invention is not limited thereto. Accordingly, any and all modifications, variations, or equivalent arrangement which may occur to those skilled in the art should be considered to be within the scope of the invention as defined in the appended claims

What is claimed is:

1. A phacoemulsification needle comprising:
    a needle body having an outside surface and an aspiration lumen therethrough;
    a hub, disposed at a proximal end of said needle body, for engaging an ultrasonic handpiece in order to couple ultrasonic energy to said needle body;
    a tip, disposed at a distal end of said needle body, for penetrating tissue to be emulsified, said tip having a larger diameter than said needle body, said tip having a tip end disposed in a plane perpendicular to a tip longitudinal axis; and
    a conical ultrasonic radiation surface, disposed in said tip, for focusing the ultrasonic energy in a converging manner in said tissue in order to break up tissue particles before the tissue particles enter said tip, the radiation surface having a maximum diameter greater than the needle body outside diameter.

2. The needle according to claim 1 wherein said conical ultrasonic radiation surface is disposed at an angle of between about 2 degrees and about 10 degrees with respect to a longitudinal axis of said needle body.

3. The needle according to claim 2 wherein said conical ultrasonic radiation surface is disposed at an angle of about 6 degrees with respect to the needle body longitudinal axis.

4. The needle according to claim 1 wherein said tip is disposed at an angle to said needle body.

5. The needle according to claim 4 wherein said tip is disposed at an angle of between about 0 degrees and about 45 degrees to said needle body.

6. A phacoemulsification needle comprising:
    a needle body having a aspiration lumen therethrough;
    a hub, disposed at a proximal end of said needle body, for engaging an ultrasonic handpiece in order to couple ultrasonic energy to said needle body;
    a tip, disposed at a distal end of said needle body, for penetrating tissue to be emulsified, said tip having a larger diameter than said needle body, said tip having a tip end disposed in a plane perpendicular to a tip longitudinal axis; and
    a conical ultrasonic radiation surface of revolution, disposed in said tip for promoting cavitation in said tissue by focusing the ultrasonic energy in a converging manner, said conical ultrasonic radiation surface extending from the lumen to the end of said tip, the tip larger diameter enabling a larger maximum diameter of the conical radiation surface, the maximum diameter being greater than an outside diameter of said needle body.

7. The needle according to claim 6 wherein said conical ultrasonic radiation surface is disposed at an angle of between about 2 degrees and about 10 degrees with respect to a longitudinal axis of said needle body.

8. The needle according to claim 7 wherein said conical ultrasonic radiation surface is disposed at an angle of about 6 degrees with respect to the needle body longitudinal axis.

9. The needle according to claim 6 wherein said tip is disposed at an angle to said needle body.

10. The needle according to claim 9 wherein said tip is disposed at an angle of between about 0 degrees and about 45 degrees to said needle body.

11. A phacoemulsification needle comprising:

a needle body having a aspiration lumen therethrough;

a hub, disposed at a proximal end of said needle body, for engaging an ultrasonic handpiece in order to couple ultrasonic energy to said needle body;

a tip, disposed at a distal end of said needle body, for penetrating tissue to be emulsified, said tip having a larger diameter than said needle body, and a conical ultrasonic radiation surface of revolution, disposed in said tip for promoting cavitation in said tissue by focusing the ultrasonic energy in a converging manner, the surface of revolution being established about a longitudinal axis of said needle body by a straight line extending between the lumen and the end of said tip, the tip larger diameter enabling a larger maximum diameter of the conical radiation surface, the tip end being disposed in a plane perpendicular to the longitudinal axis, the maximum diameter of the conical radiation surface being larger than an outside diameter of said needle body.

12. The needle according to claim 11 wherein said conical ultrasonic radiation surface is disposed at an angle of between about 2 degrees and about 10 degrees with respect to a longitudinal axis of said needle body.

13. The needle according to claim 12 wherein said conical ultrasonic radiation surface is disposed at an angle of about 6 degrees with respect to the needle body longitudinal axis.

14. The needle according to claim 13 wherein said tip is disposed at an angle to said needle body.

15. The needle according to claim 14 wherein said tip is disposed at an angle of between about 0 degrees and about 45 degrees to said needle body.

* * * * *